United States Patent [19]

Fox et al.

[11] Patent Number: 4,736,032

[45] Date of Patent: Apr. 5, 1988

[54] BENZOPYRANO[6,7,8-I,J]QUINOLIZINE-11-ONE LASING DYES AND INTERMEDIATES FOR THEIR PREPARATION

[75] Inventors: John L. Fox, Baltimore, Md.; Chin H. Chen, Webster, N.Y.

[73] Assignee: Eastman Kodak Company, Rochester, N.Y.

[21] Appl. No.: 814,460

[22] Filed: Dec. 30, 1985

[51] Int. Cl.$^4$ .................. C07D 491/06; C07D 221/06
[52] U.S. Cl. ........................................ 546/66; 546/94
[58] Field of Search ............................................ 546/66

[56] References Cited

U.S. PATENT DOCUMENTS 1,915,334  6/1933  Salzberg et al. .................. 544/59
3,873,940  3/1975  Drexhage ......................... 546/66 X

FOREIGN PATENT DOCUMENTS 3322946  1/1985  Fed. Rep. of Germany ........ 546/66

OTHER PUBLICATIONS

Reynolds et al., Chem. Abstracts, vol. 83 (1975), entry 18640g.

Mar., ed., Advanced Organic Chemistry 2nd ed, (1977), pp. 547–548.

Primary Examiner—Donald G. Daus
Assistant Examiner—William A. Teoli, Jr.
Attorney, Agent, or Firm—John R. Everett

[57] ABSTRACT

Novel benzopyrano[6,7,8-i,j]quinolizine-11-one lasing dyes and intermediates for their preparation are disclosed.

5 Claims, No Drawings

BENZOPYRANO[6,7,8-I,J]QUINOLIZINE-11-ONE LASING DYES AND INTERMEDIATES FOR THEIR PREPARATION

FIELD OF THE INVENTION

This invention relates to novel organic laser dyes and novel intermediate compounds for their preparation.

BACKGROUND OF THE INVENTION

Lasers (acronym for light amplification by stimulated emission radiation) or optical lasers (acronym for microwave amplification by stimulated emission radiation) are light amplifying devices which produce high intensity pulses of coherent monochromatic light concentrated in a well collimated beam commonly called a laser beam. There are several uses for such laser beams. Since the beam can be sharply focused, it can produce energy densities suitable for drilling, welding, cutting, etc. One potential application of laser beams is in the field of communications where the optical spectrum represents almost limitless bandwidth and information carrying capacity.

It is desirable to have lasers which are operable at many different wavelengths in the light spectrum including infrared, visible and ultraviolet regions. Since the wavelength emitted by a specific energy transmission in a laser medium is tunable over only a small portion of the spectrum, it is necessary to provide a number of materials adapted for use as active laser media at various light frequencies. Certain organic dyes in solution can operate as "liquid" or "organic dye" lasers. Of the range of materials useful as lasing media, organic lasing dyes provide certain advantages. A wide range of organic dye lasers is available to provide stimulated emission (lasing) over a broad range of the spectrum. Secondly, organic dye lasers are generally capable of being tuned to emit over a range of wavelengths. Thirdly, organic dye lasers provide an economical lasing medium when compared to gas and solid lasers, and they do not suffer from disadvantages such as cracking and optical imperfections that are particularly associated with solid lasers.

The ability to selectively tune organic dye lasers derives from the broad band fluorescence characteristic of the dye. Such lasers can be "tuned" to emit at wavelengths along substantially the entire fluorescence band of the dye by interposing a dispersive element, such as a diffraction grating or a prism.

It is known that certain unsubstituted hydroxyjulolidine dyes are capable of lasing action. However, such dyes are made in poor yields making them relatively expensive. Also, such prior art dyes are not as soluble as desired in the organic solvents most usually selected to use in the stimulated emission process. Dyes that are more soluble in organic solvents without loss of fluorescence quantum efficiency ($\Phi$) are desirable. Until now, no methods have been available to make substituted versions of such dyes.

SUMMARY OF THE INVENTION

The present invention provides a tetraalkyl-substituted benzopyrano[6,7,8-i,j]quinolizine-11-one compound comprising tetraalkyl substituents on the quinolizine group. These compounds are useful as lasing dyes as evidenced by their quantum fluorescence. They have better solubility in the required organic solvent used in lasing dye solutions. They are prepared more easily and more cheaply than the unsubstituted versions. They have the good light absorption, fluorescence and lasing properties of the unsubstituted lasing dyes.

Preferred lasing dyes of the invention have the structure

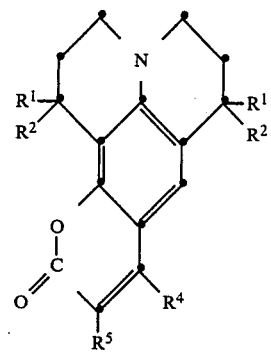

I wherein $R^1$ and $R^2$ are, each independently, lower alkyl of about 1 to 6 carbon atoms, preferably methyl;

$R^4$ represents hydrogen or lower alkyl of 1 to 6 carbon atoms such as methyl, propyl and trifluoromethyl; and $R^5$ represents hydrogen, cyano, carboxy, acyl such as acetyl, or alkoxycarbonyl such as ethoxycarbonyl and t-butoxycarbonyl.

The present invention also provides novel 1,1,7,7-alkyl-substituted 8-hydroxyjulolidines and the methanesulfonic acid salts thereof. The latter compounds are useful as intermediates in preparing the organic lasing dyes of the invention. Preferred intermediates have the structure

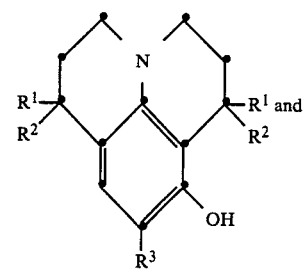

II

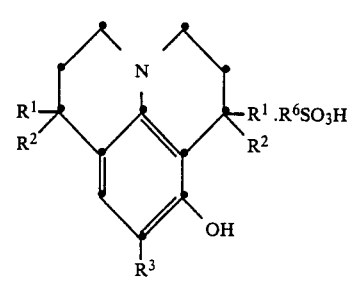

III wherein

R[1], and R[2] and R[6] each independently represent lower alkyl of about 1 to 6 carbon atoms, preferably methyl; and R[3] is —H or —CHO.

DETAILS OF THE INVENTION

The novel intermediates of this invention are made by (a) mixing m-aminophenol, N,N-dimethylformamide and calcium carbonate;

(b) adding 1-chloro-3,3-dialkyl-2-propene to the mixture at a temperature below 80° C.; p (c) adding water slowly to the mixture thereby precipitating 3-[N,N-bis(3,3-dialkyl-2-propenyl)aminophenol hydrochloride]; and (d) reacting the 3-[N,N-bis(3,3-dialkyl-2-propenyl)aminophenol hydrochloride] with an alkyl sulfonic acid to form 8-hydroxy-1,1,7,7-tetraalkyljulolidine alkyl sulfonic acid salt.

The latter alkyl sulfonic acid salt can be converted to 8-hydroxy-1,1,7,7-tetraalkyljulolidine by neutralizing the salt with a solution of sodium hydroxide. The 8-hydroxy-tetraalkyljulolidine can be converted to 9-formyl-8-hydroxy-1,1,7,7-tetraalkyljulolidine by reacting the former with a solution of phosphorous oxychloride in N,N-dimethylformamide.

The following examples will teach those skilled in the art how to make the novel intermediate compounds.

EXAMPLE 1

Step 1

Preparation of 3-[N,N-Bis(3-methyl-2-buten-1-yl)aminophenol Hydrochloride (1)

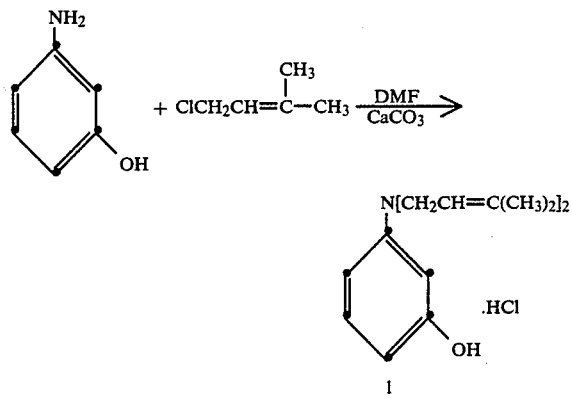

To a two-liter four-necked round-bottomed flask equipped with a nitrogen inlet, temperature probe, mechanical stirrer and a 500 mL pressure equalizing dropping funnel with an attached condenser, was added 350 mL of N,N-dimethylformamide (DMF), m-aminophenol (109.1 gm, 1.0 mole) and calcium carbonate (50 gm, 0.5 mole). The mixture was heated with a heating mantle to 65° C. and the addition funnel was charged with 1-chloro-3-methyl-2-butene (214 gm, 2.05 mole). The 1-chloro-3-methyl-2-butene was added over 15 minutes with vigorous stirring.

The temperature was kept below 80° C. by removal of the heating mantle and immersion of the flask in an ice bath when necessary. The reaction mixture was then stirred at 80° C. for 40 minutes and then cooled to room temperature by immersion of the flask in an ice bath. With vigorous stirring, 350 mL of water was added slowly through the addition funnel. After stirring for an additional 10 minutes, the precipitate was vacuum filtered through two 350 mL course sintered glass funnels. Each filter cake was washed with two 150 mL volumes of isopropyl ether. After drying for 1 hour under vacuum, the cakes were washed with an additional 150 mL of isopropyl ether. The filter cakes were dried overnight under vacuum and the solid collected to yield 124 gm (44%) of (1) as a white powder.

Step 2

Preparation of Novel Intermediate 8-Hydroxy-1,1,7,7-tetramethyljulolidine, Methylsulfonic Acid Salt(2)

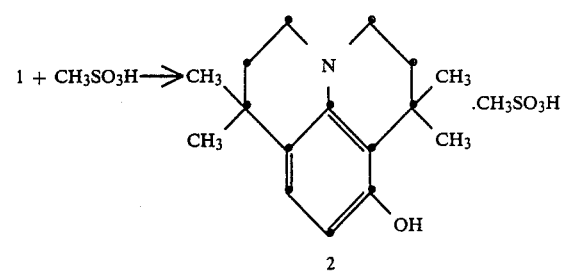

To a one liter three-necked round-bottomed flask equipped with a mechanical stirrer, nitrogen inlet and powder funnel was added 190 mL of methane sulfonic acid. Over a period of 25 minutes, 163.5 gm (0.58 mole) of the solid hydrochloride salt 1 was added with vigorous stirring. Some foaming occurs. The reaction mixture was then heated to 100° C. and maintained there for 1 hour. The reaction mixture was cooled to 40° C. with an ice bath and then poured slowly over 15 minutes into 200 mL of vigorously stirred, ice-cold water in a 1500 mL beaker immersed in an ice-acetone bath. After addition was complete, stirring was continued for an additional 15 minutes, at which time the beaker was placed in the freezer for 3 hours. The precipitate was vacuum filtered through a 1500 mL course sintered glass funnel. The filtered cake was washed twice with 100 mL volumes of ice cold water and allowed to dry overnight under vacuum. The white solid was then collected to yield 127 gm (63%) of 2. Mp 229°–30° C.; Electron impact m/e 245 (M+);

Analytical Calculation for $C_{17}H_{27}NO_4S$: C, 59.8; H, 8.0; N, 4.1; S, 9.4. Found: C, 57.6; H, 7.7; N, 3.8, S, 9.5.

EXAMPLE 2

Preparation of 8-Hydroxy-1,1,7,7-tetramethyljulolidine (3)

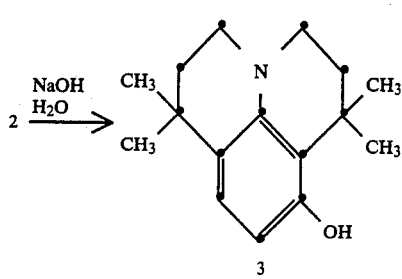

A quantity of 17.02 gm (50 mmol) of the salt 2 was added slowly to a vigorously stirred solution of 2.02 gm (50.5 mmol) of sodium hydroxide in 50 mL of water. After stirring for 5 minutes, 100 mL of ethyl acetate was added and stirring continued until both phases were clear. The organic phase was dried (MgSO$_4$) and decolorized (Norit 211 carbon). Filtration and rotary evaporation yielded 11.6 gm (94%) of 3 as a white solid. Field desorption mass spectrum: m/e 245 (M+); mp 157°–160° C.

Analytical Calculation for $C_{16}H_{23}NO$: C, 78.3; H, 9.1; N, 5.7. Found: C, 78.1; H, 9.1; N, 5.6.

EXAMPLE 3

Preparation of 9-Formyl-8-hydroxy-1,1,7,7-tetramethyljulolidine (4)

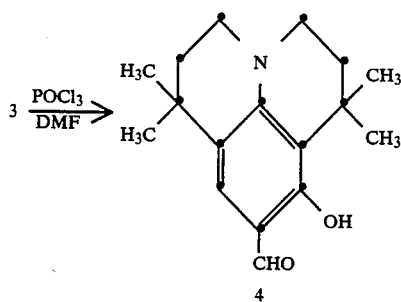

Seven mL (75 mmol) of phosphorous oxychloride was added slowly to 20 mL of N,N-dimethylformamide cooled in an ice bath. The pale yellow solution was allowed to stir at room temperature for one hour. 11.6 gm (47.0 mmol) of 3 was added portion-wise over 30 minutes, during which time the reaction mixture turned deep red. The mixture was heated at 65° C. for 6 hours and then, while still hot, poured slowly into 100 mL of vigorously stirred water. The resultant dark gum was extracted twice with 150 mL of 1:1 hexane/EtOAc. After drying and evaporating the solvent, the residual blue oil was purified by flash chromatography (6:1 hexane/EtOAc; SiO$_2$, 2×10", 175 gm). Evaporation of the solvent and drying the oil under vacuum for 2 days yielded 11.1 gm (88%) of 4 as a pale blue solid: Field desorption mass spectrum: m/e 273 (M+); mp 74°–76° C.

Analytical Calculation for $C_{17}H_{23}NO_2$: C, 74.7; H, 8.5; N, 5.1. Found: C, 74.4; H, 8.4; N, 4.9.

EXAMPLES 4–10

The novel benzopyranoquinolizinone dyes in Table I, infra, were synthesized by the following methods. Compounds 5, 6, 8 and 9 were prepared using Method A. Compounds 10 and 11 were prepared using Method B. The synthesis of Compound 7 is described after Method B.

Method A

A mixture of one equivalent of 3 from Example 2, 1.1 equivalent of the keto ester,

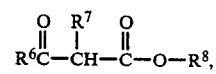

wherein $R^6$ and $R^7$ are as indicated in Table I and $R^8$ is a lower alkyl, preferably methyl, and 0.55 equivalents of anhydrous zinc chloride were mixed in a volume of absolute ethanol approximating the combined weights of the reactants. This mixture was refluxed for 14 hours, allowed to cool and poured into dilute HCl. The resulting oil was extracted twice with dichloromethane, dried (MgSO$_4$) and purified by flash chromatography (6:1 hexane/EtOAc; SiO$_2$). The solid was collected and recrystallized.

Method B

A mixture of 1.37 gm (5 mmol) of 2 from Example 1, 5.5 mmol of the ketoester used in Method A, 10 drops of piperidine and 4 mL of ethanol was refluxed for 2 hours. The solvent was removed by rotary evaporation and the residual oil recrystallized.

Preparation of Compound 7

A mixture of 1.37 gm (5 mmol) of 2 from Example 1, 0.72 gm (5 mmol) of Meldrum's acid, 10 drops of piperidine and 3 mL of absolute ethanol was refluxed for 6 hours. After cooling, the product was precipitated by slow addition of 10 mL of diethyl ether. The solid was collected and recrystallized.

TABLE I

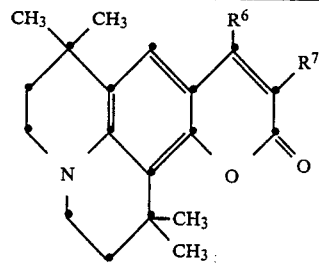

| Example No. | Compound | $R^6$ | $R^7$ | MP (°C.) | Recryst % Yield | solvent |
|---|---|---|---|---|---|---|
| 4 | 5 | H | CO$_2$CH$_2$CH$_3$ | 130–131 | 51 | hexane/ethylacetate |
| 5 | 6 | H | COCH$_3$ | 156–157 | 64 | hexane |
| 6 | 7 | H | COOH | 227–229 | 59 | hexane/ethylacetate |

TABLE I-continued

[Structure with CH3, CH3, R6, R7, N, O, CH3, CH3]

| Example No. | Compound | R6 | R7 | MP (°C.) | Recryst % Yield | solvent |
|---|---|---|---|---|---|---|
| 7 | 8 | H | COOC(CH3)3 | 158–159 | 68 | hexane |
| 8 | 9 | H | CN | 257–259 | 60 | hexane |
| 9 | 10 | CF3 | H | 106–107 | 52 | hexane |
| 10 | 11 | CF3 | H | 149–151 | 67 | hexane |

The spectra and quantum fluorescence property of the new dyes of Table I, Dyes 5-11 are given in Table II. This data shows that the dyes are useful in organic dye lasers.

The operation of a laser is achieved as a result of the phenomenon that excited atoms or molecules can emit a photon or quantum of light, which photon or quantum can itself trigger another excited atom or molecule to emit its photon prematurely. This process is designated stimulated emission. It is explained in U.S. Pat. No. 3,864,644.

Dye lasing is produced with a device having a reservoir means containing a laser dye solution and a pumping energy source capable of producing stimulated emission of the laser dye solution, the laser dye solution being a lasing concentration, in a non-interfering solvent, (i.e. one that does not inhibit stimulated emission, e.g. water, alkanols, etc.) of a 1,1,7,7-substituted 8-hydroxyjulolidine dye.

Dye solutions containing the novel dyes of the present invention can be used for lasing by employing conventional procedures, in any laser apparatus designed to employ liquid laser media, for example, the apparatus of Sorokin, mentioned previously. Further reference to useful laser apparatus appears in an article by Sorokin, Lankard, Moruzzi and Hammond, "Flashlamp-Pumped Organic Dye Lasers", *Journal of Chemical Physics*, Vol. 48.

It is generally accepted that among dyes of a particular class, those members having a higher fluorescence efficiency will be more susceptible to achieving stimulated emission under the proper conditions. Fluorescence efficiency is often meaningfully described in terms of fluorescence quantum yield. A quantum yield ($\phi$) of 1.0 means that a quantum of fluorescent light is emitted for every quantum of light absorbed by the dye. Accordingly, the quantum yield ($\phi$) is the ratio of emitted fluorescent light to absorbed light.

EXAMPLES 11–18

The following illustrative examples (Table II) are included to show the quantum fluorescence of the dyes of the present invention. The determination of fluorescence quantum yield is conveniently accomplished according to recognized procedures, such as that described in Costa, Grum and Paine, "Absolute Luminescence Spectra via Digital-Technique and Time-Resolved Spectroscopy", *Applied Optics*, Vol. 8, June 1969, p.1169; J. G. Calvert and J. N. Pitts, Jr., "Photochemistry", John Wiley and Sons, New York, NY, 1966, pp. 799–804; or C. A. Parker, "Photoluminescence of Solutions", Elsevier Publishing Co., Amsterdam, Netherlands, 1968, pp. 262–268.

TABLE II

| Compound No. | Example No. | λ-max (nm) | ε(× 10⁴) | λex, max (nm) | λem max (nm) | φ fluorescence (EtOH) |
|---|---|---|---|---|---|---|
| 5 | 11 | 436 | 4.54 | 430 | 476 | 0.79 |
| 6 | 12 | 452 | 4.60 | 452 | 494 | 0.84 |
| 7 | 13 | 418 | 3.30 | 426 | 476 | 0.52 |
| 8 | 14 | 432 | 42.4 | 432 | 476 | 0.79 |
| 9 | 15 | 440 | 4.18 | 444 | 486 | 0.80 |
| 10 | 16 | 422 | 1.97 | 430 | 532 | 0.48 |
| 10 | 17 | 420 | 1.96 | 430 | 532 | 0.50 |
| 11 | 18 | 387 | 2.14 | 388 | 464 | 0.60 |

The invention has been described in detail with particular reference to preferred embodiments thereof, but it will be understood that variations and modifications can be effected within the spirit and scope of the invention.

We claim:

1. A tetraloweralkyl substituted benzopyrano[6,7,8-i,j]quinolizine-11-one compound having two gem-diloweralkyl substituents on the quinolizine group.

2. The compound of claim 1 having the structure

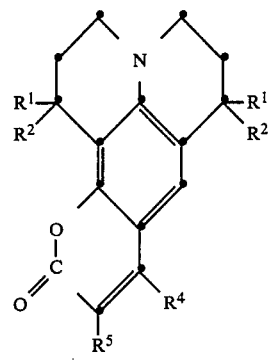

wherein
R¹ and R² each independently are lower alkyl of about 1 to 6 carbon atoms;
R⁴ represents hydrogen or alkyl; and
R⁵ represents hydrogen, cyano, carboxy, lower alkanoyl, or alkoxycarbonyl.

3. The compound of claim 2 having the structure

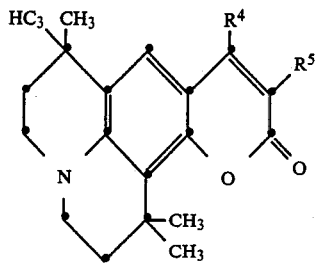

wherein

R⁴ represents hydrogen or methyl; and

R⁵ represents hydrogen, cyano, carboxy, lower alkanoyl, or alkoxycarbonyl.

4. A compound according to claim 2 having the structure

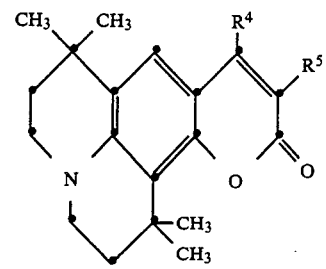

wherein
R⁴ represents —H, —CF₃ or —CH₃; and
R⁵ represents —H, —COOC₂H₅, —COOCH₃, —COOC(CH₃)₃, —COOH and —CN.

5. A compound according to claim 2 selected from Table I as follows:

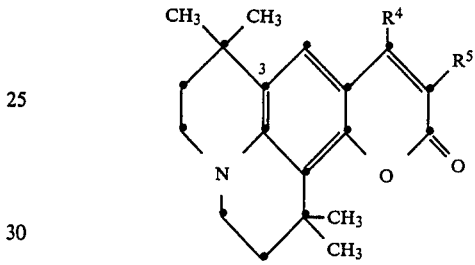

| Example No. | Compound | R⁴ | R⁵ |
|---|---|---|---|
| 4 | 5 | H | —CO₂C₂H₅ |
| 5 | 6 | H | —CO₂CH₃ |
| 6 | 7 | H | —COOH |
| 7 | 8 | H | COOC(CH₃)₃ |
| 8 | 9 | H | CN |
| 9 | 10 | CF₃ | H |
| 10 | 11 | CH₃ | H |

\* \* \* \* \*